US00PP25955P3

(12) United States Plant Patent
Morales

(10) Patent No.: US PP25,955 P3
(45) Date of Patent: Sep. 29, 2015

(54) ***LANTANA* PLANT NAMED 'MANUEL'S RED'**

(50) Latin Name: *Lantana camara*
Varietal Denomination: MANUEL'S RED

(71) Applicant: Manuel Morales, Royal Oaks, CA (US)

(72) Inventor: Manuel Morales, Royal Oaks, CA (US)

( * ) Notice: Subject to any disclaimer, the term of this patent is extended or adjusted under 35 U.S.C. 154(b) by 54 days.

(21) Appl. No.: 13/999,017

(22) Filed: Dec. 31, 2013

(65) Prior Publication Data

US 2015/0189806 P1 Jul. 2, 2015

(51) Int. Cl.
*A01H 5/00* (2006.01)

(52) U.S. Cl.
USPC ..... Plt./227

(58) Field of Classification Search
USPC ..... Plt./227
CPC ..... A01H 5/02; A01H 5/00
See application file for complete search history.

*Primary Examiner* — Kent L Bell
(74) *Attorney, Agent, or Firm* — Cassandra Bright

(57) ABSTRACT

A new and distinct *Lantana* cultivar named 'MANUEL'S RED' is disclosed, characterized by distinctive variegated foliage and solid red flowers. The new variety is a *Lantana*, normally produced as an outdoor garden or container plant.

1 Drawing Sheet

Latin name of the genus and species: *Lantana camara.*
Variety denomination: 'MANUEL'S RED'.

BACKGROUND OF THE INVENTION

The new *Lantana* cultivar is a product of a chance discovery by the inventor, Manuel Morales. The new variety was discovered as a naturally occurring single branch mutation of the variety *Lantana camara* 'Radiation Improved', unpatented.

Mr. Morales discovered the new variety in a commercial planting of the parent variety at his nursery in Royal Oaks, Calif. during the Fall of 2010.

Asexual reproduction of the new cultivar 'MANUEL'S RED' by vegetative cuttings was first performed at a commercial nursery in December 2010. Subsequently, several generations have been produced, and have shown that the unique features of this cultivar are stable and reproduced true to type in successive generations.

SUMMARY OF THE INVENTION

The cultivar 'MANUEL'S RED' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MANUEL'S RED' These characteristics in combination distinguish 'MANUEL'S RED' as a new and distinct *Lantana* cultivar:

1. Bright red flower color
2. Semi-upright outwardly spreading plant habit
3. Variegated foliage

PARENT COMPARISON

Plants of the new cultivar 'MANUEL'S RED' are comparable to the parent *Lantana camara* 'Radiation Improved', unpatented. The two *Lantana* varieties are similar in most horticultural characteristics however, the new variety 'MANUEL'S RED' differs in having variegated foliage, whereas 'Radiation Improved' has solid green foliage. Flower color of the new variety is typically solid red, whereas 'Radiation Improved' varies in flower color.

COMMERCIAL COMPARISON

Plants of the new cultivar 'MANUEL'S RED' are comparable to the variety *Lantana camara* 'Dallas Red', unpatented. The two *Lantana* varieties are similar in most horticultural characteristics however, the new variety 'MANUEL'S RED' differs in having variegated foliage, whereas 'Dallas Red' had solid green foliage.

Plants of the new cultivar 'MANUEL'S RED' are comparable to the commercial variety *Lantana* 'Pink Lemonade' unpatented. The two *Lantana* varieties are similar in most horticultural characteristics, including the characteristic of variegated foliage. Plants of the new variety 'MANUEL'S RED', however, have red flowers, whereas flowers of 'Pink Lemonade' are pink and yellow.

BRIEF DESCRIPTION OF THE PHOTOGRAPH

FIG. 1: Illustrates in full color a closeup view of foliage of 'Manuel's Red'.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MANUEL'S RED' plants grown approximately 30 weeks outdoors in Royal Oaks, Calif. The growing temperature ranged from 10° C. to 20° C. during the night and from 15° C.

to 35° C. during the day. General light conditions are bright, normal sunlight. Measurements and numerical values represent averages of typical plant types.

Botanical classification: *Lantana camara* 'MANUEL'S RED'.

PROPAGATION

Time to initiate roots: 6 to 8 days at approximately 15° C.

Root description: Fibrous.

PLANT

Growth habit: Spreading.

Pot size of plant described: 1 gallon.

Height: 30 cm.

Plant spread: 45 cm.

Growth rate: Rapid.

Branching characteristics: Freely Branches at each internode with two lateral branches.

Length of primary lateral branches: Average 33 cm.

Diameter of lateral branches: 0.7 cm.

Quantity of primary lateral branches: 4.

Characteristics of primary lateral branches:

*Form*.—Round.

*Diameter*.—0.3 cm.

*Color*.—Near Yellow-Green 144B at tip changing to Greyed-Green 197B and 197C.

*Texture*.—Pubescent, becoming scaly with age.

*Strength*.—Soft/Very Flexible when young, woody and more brittle with age.

Internode length: 2 to 4 cm.

FOLIAGE

Leaf:

*Arrangement*.—Opposite.

*Quantity*.—Approximately 14-18 per branch.

*Average length*.—3.5 cm.

*Average width*.—1.8 cm.

*Shape of blade*.—Ovate.

*Apex*.—Acute.

*Base*.—Attenuate.

*Margin*.—Serrated.

*Texture of top surface*.—Pubescent.

*Texture of lower surface*.—Pubescent.

*Aspect*.—Flat.

*Color*.—Young foliage upper side: Near RHS Green 137A with Yellow-Green 145B variegation. Young foliage under side: Near RHS Green 137A with Yellow-Green 145B variegation. Mature foliage upper side: Near RHS Green 137A with Yellow-Green 1MC variegation. Mature foliage under side: Near RHS Green 137A with Green-Yellow 1B variegation.

*Venation*.—Type: Pinnate. Venation color upper side: Indistinguishable from leaf blade. Venation color under side: Indistinguishable from leaf blade.

*Petiole*.—Length: 0.4 cm. Diameter: 0.15 cm. Color: Near RHS Yellow-Green 144C. Texture: Slightly Pubescent.

FLOWER

Natural flowering season: Continuous Flowers in Warm Climate.

Days to flowering from rooted cutting: Approximately 28.

Inflorescence and flower type and habit: Corymb.

Rate of flower opening: 4 to 5 days from bud to fully opened flower.

Flower longevity on plant: 8-10 days.

Persistent or self-cleaning: Self Cleaning.

Overall inflorescence size:

*Height*.—Approximately 1.0 cm.

*Diameter*.—Approximately 3.0 cm.

Individual flower size:

*Height*.—Approximately 1.1 cm including corolla tube.

*Diameter*.—Approximately 0.9 cm.

Bud:

*Shape*.—Squared tubular.

*Length*.—1.0 cm Including corolla tube.

*Diameter*.—0.3 cm.

*Color*.—Near RHS Red 45B.

Corolla:

*Petals/lobes*.—Number: 4. Length: 0.5 cm upper — 0.6 cm lower — 0.5 cm lateral petals. Width: 0.5 cm upper — 0.7 cm lower — 0.4 cm lateral petals. Shape: Salverform. Aspect: Slightly cupped with a long slender tube. Margin: Entire. Texture: Glabrous to somewhat velvety.

*Color*.—When opening: Upper surface: Near RHS Red 45B. Lower surface: Near RHS Red 45B. Fully opened: Upper surface: Near RHS Red 45B. Lower surface: Near RHS Red 45B.

*Throat/tube*.—Color: Near RHS Red 45B, inner and outer surfaces. Texture: Smooth.

*Calyx/sepals*.—Form: 5 Fused Sepals. Length: 0.3 cm. Diameter: 0.1 cm. Sepal shape: 5 Fused Sepals Form a Tube. Sepal margin: Fused. Sepal texture: Smooth. Sepal color: Upper surface: Yellow-Green 144A. Lower surface: Yellow-Green 144B.

Flower bracts/inflorescence bracts:

*Appearance*.—Matte.

*Length*.—Approximately 0.7 cm.

*Width*.—Approximately 0.1 cm.

*Shape*.—Narrow deltoid.

*Aspect*.—Cupped.

*Apex*.—Acute.

*Margin*.—Entire.

*Texture*.—Upper (inner) and lower (outer) surfaces: Glabrous.

*Color*.—Upper (inner) and lower (outer) surfaces:

*Upper*.—Green 137C — Lower — Green 137C.

Peduncles:

*Length*.—Average 1.7 cm.

*Diameter*.—Approximately 0.1 cm.

*Angle*.—About 35 degrees.

*Strength*.—Strong.

*Texture*.—Pubescent.

*Color*.—Yellow-Green 144A.

*Flower fragrance*.—Faint.

REPRODUCTIVE ORGANS

Stamens:

*Number* (*per flower*).—4.

*Filament length.*—0.1 cm.

*Anthers*.—Shape: Ovate. Length: 0.1 cm. Color: Brown 200A.

Pollen: Color: Near RHS Greyed-Orange 163A. Amount: Sparse To None.

Pistils:

*Quantity per flower.*—1.

*Length.*—0.4 cm.

*Styles*.—Length: 0.3 cm. Color: Yellow-Green 144B.

*Ovary color*.—Green 137D.

*Stigma*.—Shape: Oval. Color: Yellow-Green 144A.

OTHER CHARACTERISTICS

Seed: Very little seed produced.

*Seed diameter*.—0.1 cm. Seed Color: Black 202A.

Fruit: Drupe.

*Young fruit*.—Drupe; Diameter: 0.3 cm. Color: Yellow-Green 146A.

*Older fruit*.—Diameter: 0.2 cm. Color: Black 202A.

Disease/pest resistance: Neither resistance nor susceptibility to pathogens and pests common to *Lantana* have been observed.

Temperature tolerance: The new variety tolerates temperatures between 0 to 40° C.

What is claimed is:

1. A new and distinct cultivar of *Lantana* plant named 'MANUEL'S RED' as herein illustrated and described.

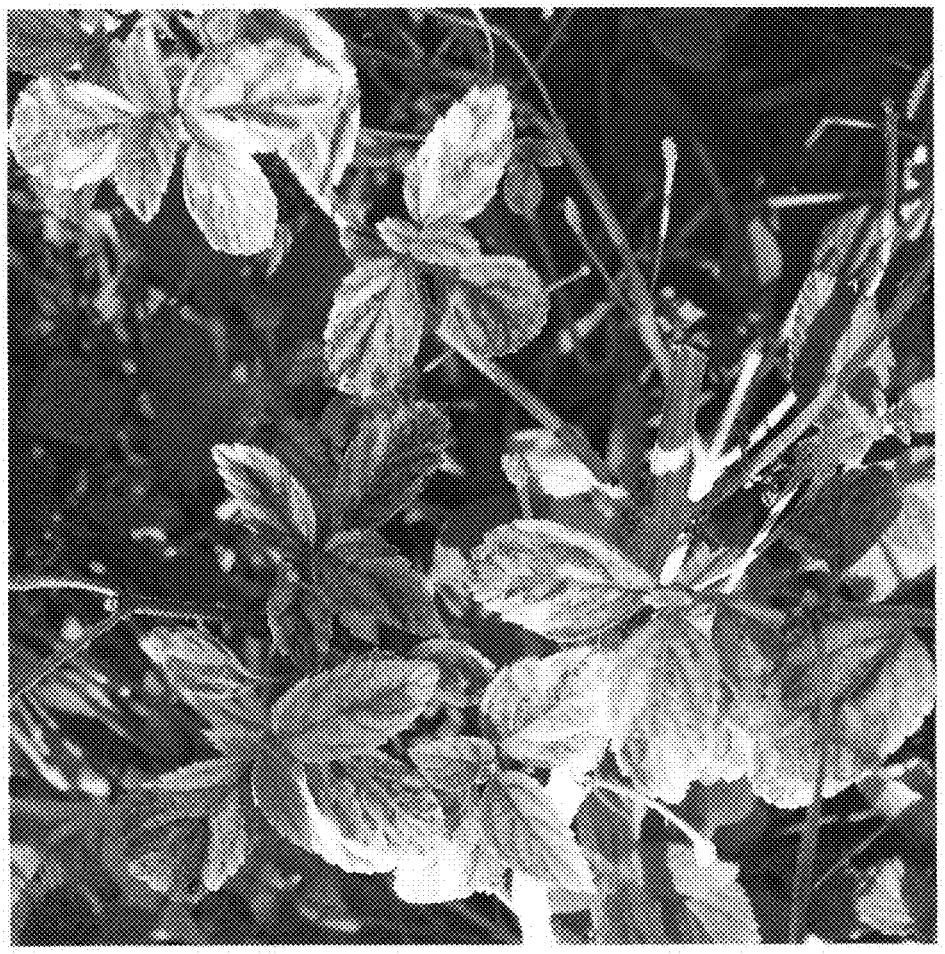

* * * * *